(12) United States Patent
Hembrough et al.

(10) Patent No.: US 9,746,477 B2
(45) Date of Patent: Aug. 29, 2017

(54) QUANTIFYING FR-α AND GART PROTEINS FOR OPTIMAL CANCER THERAPY

(71) Applicant: Expression Pathology, Inc., Rockville, MD (US)

(72) Inventors: Todd Hembrough, Gaithersburg, MD (US); Fabiola Cecchi, Bethesda, MD (US); Eunkyung An, Bethesda, MD (US); Manish Monga, Wheeling, WV (US)

(73) Assignees: Expression Pathology, Inc., Rockville, MD (US); West Virginia University, Morgantown, WV (US)

( * ) Notice: Subject to any disclaimer, the term of this patent is extended or adjusted under 35 U.S.C. 154(b) by 0 days.

(21) Appl. No.: 15/225,824

(22) Filed: Aug. 1, 2016

(65) Prior Publication Data

US 2017/0030923 A1    Feb. 2, 2017

Related U.S. Application Data

(60) Provisional application No. 62/199,202, filed on Jul. 30, 2015.

(51) Int. Cl.
| | |
|---|---|
| *A61K 31/519* | (2006.01) |
| *A61K 31/28* | (2006.01) |
| *G01N 33/68* | (2006.01) |
| *A61K 33/24* | (2006.01) |

(52) U.S. Cl.
CPC ....... *G01N 33/6848* (2013.01); *A61K 31/519* (2013.01); *A61K 33/24* (2013.01); *G01N 2333/705* (2013.01); *G01N 2333/9015* (2013.01)

(58) Field of Classification Search
CPC ............................. A61K 31/519; A61K 31/28
USPC .................................................. 514/519, 492
See application file for complete search history.

(56) References Cited

U.S. PATENT DOCUMENTS

| | | | | |
|---|---|---|---|---|
| 7,053,065 | B2 * | 5/2006 | Niyikiza ............ | A61K 31/519 514/249 |
| 2007/0117815 | A1 * | 5/2007 | Pluda .................. | A61K 31/167 514/265.1 |
| 2008/0306094 | A1 * | 12/2008 | Wedge ............... | A61K 31/4985 514/265.1 |
| 2011/0201631 | A1 * | 8/2011 | Kocherlakota ......... | A61K 9/19 514/265.1 |

* cited by examiner

*Primary Examiner* — Raymond Henley, III
(74) *Attorney, Agent, or Firm* — Edell, Shapiro & Finnan, LLC

(57) ABSTRACT

Improved methods are provided for treating cancer patients, particularly patients suffering from lung cancer. Methods are provided for identifying whether a lung tumor will be responsive to treatment with a therapeutic regimen that includes pemetrexed and optionally includes cisplatin. A specific FR-α fragment peptide and a specific GART fragment peptide are precisely detected and quantitated by SRM-mass spectrometry directly in lung tumor cells collected from lung tumor tissue that was obtained from a cancer patient and compared to reference levels in order to determine if the lung cancer patient will positively respond to treatment with the c therapeutic regimen.

17 Claims, 6 Drawing Sheets

QUANTIFYING FR-α AND GART PROTEINS FOR OPTIMAL CANCER THERAPY

This application claims the benefit of U.S. Provisional Application No. 62/199,202 filed Jul. 30, 2015, entitled "Quantifying FR-α and GART Proteins for Optimal Cancer Therapy,"the contents of which is hereby incorporated by reference in its entirety. This application also contains a sequence listing submitted electronically via EFS-web, which serves as both the paper copy and the computer readable form (CRF) and consists of a file entitled "001152 8048 US01 SEQ LISTING", which was created on Sep. 13, 2016, which is 1,146 bytes in size, and which is also incorporated by reference in its entirety.

INTRODUCTION

New and improved methods for treating cancer patients are provided. The methods measure the levels of specific proteins in tumor tissue from patients and then, based upon those levels, treat the patients with an optimized medication regimen. More specifically, the methods allow a treating physician to identify whether or not a patient will respond to, or is likely to respond to, treatment with a therapeutic regimen that includes the anti-cancer drug pemetrexed, and/or other anti-cancer drugs in the antifolate class of drugs such as lometrexol, AG2034, LY309887 and pelitrexol that function to kill tumor cells in a similar manner by attacking the GART protein.

Pemetrexed is a member of the antifolate class of drugs that enter the tumor cell via the Folate Receptor-alpha (FR-α), the Receptor-beta (FR-β), proton-coupled folate transporter (PCFT), and the Folate transporter 1 (RFC). Once inside the tumor cell the biochemical mode of action of these drugs is to inhibit glycinamide ribonucleotide synthetase (GART) protein function, and the function of other cellular proteins including thymidylate synthase (TS) and dihydrofolate reductase (DHFR). This inhibition results in the tumor cell being unable to synthesize nucleic acids, which prevents cell division and ultimately kills the tumor cells. Presence of the FR-α in tumor cells mediates active uptake of pemetrexed (and similar drugs) into the tumor cells, while reliance on the GART protein (and other proteins such as TS and DHFR) for tumor cell growth and division is interrupted by the biochemical function of pemetrexed.

The presence and/or quantitative levels of FR-α and GART protein expression in the tumor tissue is determined by quantitating a specified peptide derived from subsequences of the full-length 257 amino acid FR-α protein (also referred to as Folate receptor alpha, Adult folate-binding protein, FBP, Folate receptor, Folate receptor-adult, and Ovarian tumor-associated antigen MOv18) and subsequences of the full-length 433 amino acid GART protein (also referred to as Trifunctional purine biosynthetic protein adenosine-3, GAR transformylase, 5'-phosphoribosylglycinamide transformylase, Phosphoribosylglycinamide formyltransferase, PGFT, PRGS, Glycinamide ribonucleotide synthetase, GARS, GARFT, AIR synthase, and AIRS). If expression of the FR-α protein is detected and specific levels of the GART protein is found below a specified quantitative level, the patient is treated with a regimen that includes the pemetrexed therapeutic agent, and other drugs that function similarly to pemetrexed. Alternatively, if the FR-α level is below the level of detection and levels of the GART protein are found to be above a specified quantitative level, the patient is treated with a regimen that does not include pemetrexed therapeutic agent, nor other drugs that function similarly such as lometrexol, AG2034, LY309887 and pelitrexol.

The specified FR-α and GART peptides are detected using mass spectrometry-based Selected Reaction Monitoring (SRM), also referred to as Multiple Reaction Monitoring (MRM), and referred to herein as an SRM/MRM assay. An SRM/MRM assay is used to detect the presence and quantitatively measure the amount of the specified FR-α and GART fragment peptides, directly in cells procured from cancer patient tissue, such as, for example formalin fixed cancer tissue. The amount of the specific peptides is then used to quantitate the amount of intact FR-α and GART proteins in the tumor sample. Specific and optimized therapeutic agents and treatment strategies are then determined and implemented to treat an individual cancer patient's disease based on how much of the FR-α and GART proteins are present in their cancer cells.

SUMMARY OF THE INVENTION

What is provided is a method of treating a patient suffering from lung cancer, where the method comprises quantifying the level of a specified FR-α fragment peptide and the level of a specified GART fragment peptide in a protein digest prepared from a tumor sample obtained from the patient and calculating the level of both the FR-α and GART peptides in said sample by selected reaction monitoring using mass spectrometry; comparing the level of the FR-α fragment peptide to an FR-α reference level and comparing the level of the GART fragment peptide to a GART reference level, and then treating the patient with a therapeutic regimen that includes an effective amount of pemetrexed when the level of the GART fragment peptide is lower than the reference level and when the level of the FR-α fragment peptide is detected, or treating the patient with a therapeutic regimen that does not contain an effective amount of pemetrexed when the level of the GART fragment peptide is above the reference level and the FR-α fragment peptide is not detected. When the therapeutic regimen includes pemetrexed is may also optionally include an effective amount of cisplatin.

In these methods the reference level of the GART fragment peptide may be 900 amol/μg., +/−250 amol/μg, +/−150 amol/μg, +/−100 amol/μg, +/−50 amol/μg, or +/−25 amol/μg of biological sample protein analyzed and when the FR-α fragment peptide is detected above the lower limit of detection or not detected.

The protein digest may be a protease digest, for example a trypsin digest. The mass spectrometry may be a method such as tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry. The mode of mass spectrometry used may be, for example, Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

The specified FR-α peptide may have the amino acid sequence as set forth as SEQ ID NO:1 and/or the specified GART peptide may have the amino acid sequence as set forth as SEQ ID NO:2.

The tumor sample may be a cell, collection of cells or, advantageously, a solid tissue, such as formalin fixed solid tissue, and optionally may be paraffin embedded formalin-fixed tissue. The protein digest of the biological sample may be prepared by the Liquid Tissue protocol as described, for example, in U.S. Pat. No. 7,473,532.

In the methods described above, quantifying the specified FR-α fragment peptide may, for example, be carried out by comparing to a spiked internal standard peptide of known amount, where both the native peptide in the biological sample and the internal standard peptide corresponds to the same amino acid sequence of the FR-α fragment peptide as shown in SEQ ID NO:1. Quantifying the specified GART fragment peptide may be carried out by comparing to a spiked internal standard peptide of known amount, where both the native peptide in the biological sample and the internal standard peptide corresponds to the same amino acid sequence of the GART fragment peptide as shown in SEQ ID NO:2. In these methods the internal standard peptide may be an isotopically labeled peptide, and may comprise at least one heavy stable isotope selected from $^{18}O$, $^{17}O$, $^{15}N$, $^{13}C$, and $^{2}H$, or combinations thereof. Optionally, detecting and quantitating the specified FR-α fragment peptide and/or the GART fragment peptide can be combined with detecting and quantitating other peptides from other proteins in multiplex so that the treatment decision about which agent used for treatment is based upon specific levels of the specified FR-α fragment peptide and GART peptide respectively in combination with other peptides/proteins in the biological sample.

DETAILED DESCRIPTION

Figure 1:
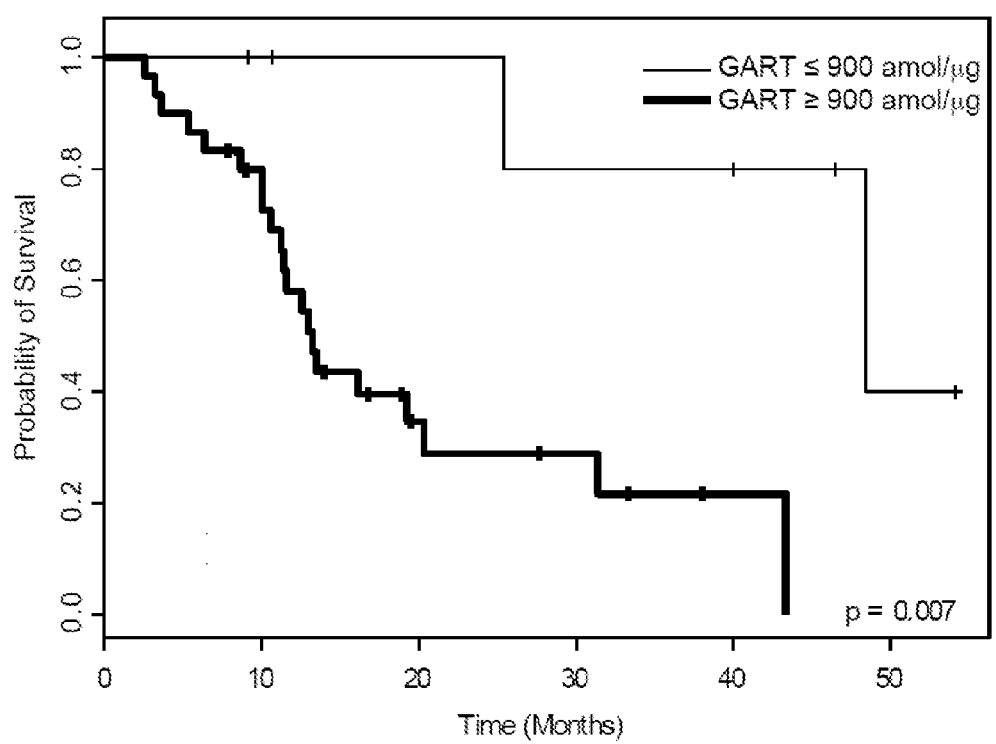
FIG. 1 shows the overall survival curve for patients whose tumor cells express levels of the GART protein below 900 amol/μg of protein analyzed. These patients have a much greater probability of longer overall survival than patients whose tumor cells express above 900 amol/μg of protein analyzed when treated with the therapeutic combination of pemetrexed and cisplatin.

Methods are provided for identifying and optimizing treatment strategies for a cancer patient by determining whether or not a cancer patient will clinically respond in a favorable manner to the therapeutic cancer agent pemetrexed. Pemetrexed is also referred to as Alimta®. Specifically, diagnostic methods for measuring the combination of the FR-α and GART proteins in a tumor sample or samples from the patient are provided. The tumor sample is advantageously a formalin-fixed tissue sample.

Using an SRM/MRM assay that simultaneously measures a combination of specific FR-α and GART peptide fragments, and particular characteristics about the peptides, the amount of the FR-α and GART proteins in cells derived from formalin fixed paraffin embedded (FFPE) tissue is determined. The peptide fragments derive from the full-length FR-α and GART proteins; advantageously, the specific peptide sequence that is used for FR-α is DVSYLYR (SEQID NO:1) and the peptide sequence used for detecting and quantitating the GART protein is VLAVTAIR (SEQ ID NO:2). Detection and accurate quantitation of specific peptides from FR-α and GART proteins in digests of FFPE tissue is highly unpredictable, due to the random protein crosslinking that occurs during formalin fixation of proteins. Surprisingly, however, it has been found that these specific FR-α and GART peptides can be reliably detected and quantitated simultaneously in digests prepared from FFPE samples of tumor tissue. See U.S. patent application Ser. No. 13/993,045, the contents of which are hereby incorporated by reference in their entirety.

More specifically, this SRM/MRM assay can measure these peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by reference in their entirety. The methods described in U.S. Pat. No. 7,473,532 may conveniently be carried out using Liquid Tissue reagents and protocol available from Expression Pathology Inc. (Rockville, Md.).

The most widely and advantageously available form of tissue, and cancer tissue, from cancer patients is formalin fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (about 40% by volume or 37% by mass) in water. A small amount of stabilizer, usually methanol, is added to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature.

Results from the SRM/MRM assay can be used to correlate accurate and precise quantitative levels of both the FR-α and GART proteins within the specific cancer of the patient from whom the tissue was collected and preserved, including lung cancer tissue. This not only provides diagnostic information about the cancer, but also permits a physician or other medical professional to determine appropriate therapy for the patient. In this case, utilizing this assay can provide information about specific levels of both FR-α and GART protein expression in cancer tissue from a patient and makes it possible to determine whether or not the patient will respond favorably to therapy with the anti-cancer therapeutic agent pemetrexed, and potentially with other similar drugs in the antifolate class, designed to specifically inhibit the function of the GART, TS, and/or DHFR proteins.

Treating cancer patients with pemetrexed is one of the most common and effective strategies for preventing cancer from growing and thus prolonging the lives of cancer patients, especially lung cancer patients. The FR-α protein is a receptor protein that is abnormally present on many types of tumor cells, including lung cancer cells. Normally the FR-α protein brings folate and reduced folic acid derivatives into a cell which helps control how a healthy normal cell grows, divides, and repairs itself. However, in some cancers, including lung cancer, the cancer cells abnormally express FR-α protein and the cancer cells grow and divide in an uncontrolled way. It therefore is very useful for a clinician to know if the FR-α protein is present in a patient's cancer cells because the pemetrexed agent enters the cancer cell via the FR-α protein. The GART protein is a multifunctional transferase/ligase protein that is involved in purine metabolism and thus is an integral part of the nucleic acid synthesis function of the cell, and without which the cell cannot synthesize nucleic acids and grow/divide. Accordingly, inhibiting the function of the GART protein with pemetrexed prevents the tumor cell from synthesizing nucleic acids and leads to tumor cell death. It therefore is useful for a clinician to know the level of the GART protein is in a patient's tumor cells to determine if pemetrexed will have a toxic effect on the tumor cells.

The most widely-used methodology presently applied to determine protein presence in cancer patient tissue, especially FFPE tissue, is immunohistochemistry (IHC). IHC methodology uses an antibody to detect the protein of interest. The results of an IHC test are most often interpreted by a pathologist or histotechnologist. This interpretation is subjective and does not provide quantitative data that are predictive of sensitivity to therapeutic agents that target specific oncoprotein targets. Thus, an IHC test cannot determine whether or not an FR-α and GART positive tumor cell population will be sensitive to treatment with pemetrexed.

Studies involving other IHC assays, such as the Her2 IHC test, suggest the results obtained from such tests may be wrong or misleading. This is likely because different laboratories use different rules for classifying positive and negative IHC status. Each pathologist running a test also may use different criteria to decide whether the results are positive or negative. In most cases, this happens when the test results are borderline, i.e. the results are neither strongly positive nor strongly negative. In other cases, tissue from one area of cancer tissue can test positive while tissue from a different area of the cancer tests negative.

Inaccurate IHC test results may mean that patients diagnosed with cancer do not receive the best possible care. If all or part of a cancer is positive for a specific target oncoprotein but test results classify it as negative, physicians are unlikely to implement the correct therapeutic treatment, even though the patient could potentially benefit from agents that target the oncoprotein. If a cancer is oncoprotein target negative but test results classify it as positive, physicians may use a specific therapeutic treatment, even though the patient is not only unlikely to receive any benefit but also is exposed to the agent's secondary risks.

Thus there is great clinical value in the ability to correctly evaluate quantitative levels of the FR-α and GART proteins in tumors, especially lung tumors, so that the patient will have the greatest chance of receiving a successful treatment regimen while reducing unnecessary toxicity and other side effects.

Detection of peptides and determining quantitative levels of specified FR-α and GART fragment peptides are determined in a mass spectrometer by the SRM/MRM methodology, in which the SRM/MRM signature chromatographic peak area of each peptide is determined within a complex peptide mixture present in a Liquid Tissue lysate (see U.S. Pat. No. 7,473,532, as described above). Quantitative levels of the FR-α and GART proteins are then determined by the SRM/MRM methodology whereby the SRM/MRM signature chromatographic peak area of an individual specified peptide from each of the FR-α and GART proteins in one biological sample is compared to the SRM/MRM signature chromatographic peak area of a known amount of a "spiked" internal standard for each of the individual specified FR-α and GART fragment peptides.

In one embodiment, the internal standard is a synthetic version of the same exact FR-α and GART fragment peptides where the synthetic peptides contain one or more amino acid residues labeled with one or more heavy isotopes, such as $^2$H, $^{18}$O, $^{17}$O, $^{15}$N, $^{13}$C, or combinations thereof. Such isotope labeled internal standards are synthesized so that mass spectrometry analysis generates a predictable and consistent SRM/MRM signature chromatographic peak that is different and distinct from the native FR-α and GART fragment peptide chromatographic signature peaks and which can be used as comparator peaks. Thus when the internal standard is "spiked" in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

In order to develop the SRM/MRM assay for the FR-α and GART fragment peptides additional information beyond simply the peptide sequence needs to be utilized by the mass spectrometer. That additional information is used to direct and instruct the mass spectrometer, (e.g., a triple quadrupole mass spectrometer) to perform the correct and focused analysis of the specified FR-α and GART fragment peptides. An SRM/MRM assay may be effectively performed on a triple quadrupole mass spectrometer. That type of a mass spectrometer may be considered to be one of the most suitable instruments for analyzing a single isolated target peptide within a very complex protein lysate that may consist of hundreds of thousands to millions of individual peptides from all the proteins contained within a cell. The additional information provides the mass spectrometer, such as a triple quadrupole mass spectrometer, with the correct directives to allow analysis of a single isolated target peptide within a very complex protein lysate. SRM/MRM assays also can be developed and performed on other types of mass spectrometer, including MALDI, ion trap, ion trap/quadrupole hybrid, or triple quadrupole instruments, but presently the most advantageous instrument platform for SRM/MRM assay is often considered to be a triple quadrupole instrument platform. The additional information about target peptides in general, and in particular about the specified FR-α (SEQ ID NO:1) and GART (SEQ ID NO:2) fragment peptides, may include one or more of the mono isotopic mass of each peptide, its precursor charge state, the precursor m/z value, the m/z transition ions, and the ion type of each transition ion. The peptide sequence of the specified FR-α and GART fragment peptides and the necessary additional information as described for these specified FR-α and GART fragment peptides is shown in Table 1.

TABLE 1

| SEQ ID | Peptide sequence | Mono Isotopic Mass | Precursor Charge State | Precursor m/z | Transition m/z | Ion Type |
|---|---|---|---|---|---|---|
| FR-α | | | | | | |
| SEQ ID NO: 1 | DVSYLYR | 916.021 | 2 | 458.511 | 451.266 | y3 |
| | | | 2 | 458.511 | 614.329 | y4 |
| | | | 2 | 458.511 | 701.361 | y5 |
| GART | | | | | | |
| SEQ ID NO: 2 | VLAVTAIR | 841.5385 | 2 | 421.7765 | 359.2396 | y3 |
| | | | 2 | 421.7765 | 460.2873 | y4 |
| | | | 2 | 421.7765 | 559.3557 | y5 |
| | | | 2 | 421.7765 | 630.3928 | y6 |
| | | | 2 | 421.7765 | 743.4769 | y7 |

To determine an appropriate reference level for FR-α and GART quantitation, tumor samples were obtained from a cohort of patients suffering from cancer, in this case lung cancer. The lung tumor samples were formalin-fixed using standard methods and the level of FR-α and GART in the samples was measured using the methods as described above. The tissue samples may also be examined using IHC and FISH using methods that are well known in the art. The patients in the cohort were treated with the pemetrexed therapeutic agent and the response of the patients was measured using methods that are well known in the art, for example by recording the overall survival of the patients at time intervals after treatment. A suitable reference level was determined using statistical methods that are well known in the art, for example by determining the lowest p value of a log rank test. Once a reference level was determined it was used to identify those patients whose FR-α and GART expression levels indicate that they may likely benefit from a pemetrexed therapeutic regimen.

The skilled artisan will recognize that pemetrexed may also be used as part of a treatment regimen that includes additional drugs or combinations of drugs, such as a combination with the drug cisplatin. Therapeutic regimens for treating lung cancer are known in the art and a very common and widely-used drug combination is cisplatin combined with pemetrexed. Levels of FR-α and GART proteins in patient tumor samples are typically expressed in amol/μg, although other units can be used. The skilled artisan will recognize that a reference level can be expressed as a range around a central value, for example, +/−250, 150, 100, 50 or 25 amol/μg. In the specific example described in detail below a suitable reference level for the GART protein was found to be 900 amol/μg while a suitable reference level for the FR-α protein was found to be 400 amol/μg which is the lower limit of detection. However, the skilled artisan will recognize that levels higher or lower than these reference levels can be selected based on clinical results and experience.

Because both nucleic acids and protein can be analyzed from the same Liquid Tissue biomolecular preparation it is possible to generate additional information about disease diagnosis and drug treatment decisions from the nucleic acids in same sample upon which proteins were analyzed. For example, if the FR-α and GART proteins are expressed by certain cells at increased levels, when assayed by SRM the data can provide information about the state of the cells and their potential for uncontrolled growth, choice of optimal therapy, and potential drug resistance. At the same time, information about the status of genes and/or the nucleic acids and proteins they encode (e.g., mRNA molecules and their expression levels or splice variations) can be obtained from nucleic acids present in the same Liquid Tissue™ biomolecular preparation. Nucleic acids can be assessed simultaneously to the SRM analysis of proteins, including the FR-α and GART proteins. In one embodiment, information about the FR-α and GART proteins and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

EXAMPLE

Determination of a Predictive Value of FR-α and GART Protein Expression Levels for Pemetrexed Sensitivity in a Population of Lung Cancer Patients Patients 37 patients were identified with non-small cell lung cancer (NSCLC). Tumors were surgically removed prior to treatment and archived as formalin-fixed, paraffin-embedded (FFPE) tissue and all were histologically confirmed as adenocarcinoma. All 37 patients were subsequently treated with the standard combination chemotherapy regimen of cisplatin and pemetrexed.

Methods

Tumor cells from FFPE tumor tissue were procured and isolated from the tumor tissue by tissue microdissection and solubilized for downstream mass spectrometry analysis using the Liquid Tissue reagents as described above. Protein levels were quantitated using selected reaction monitoring mass spectrometry (SRM-MS). Overall survival curves of the patients in this study as related to levels of various proteins, including FR-α and GART proteins were developed.

Results

Figure 2:
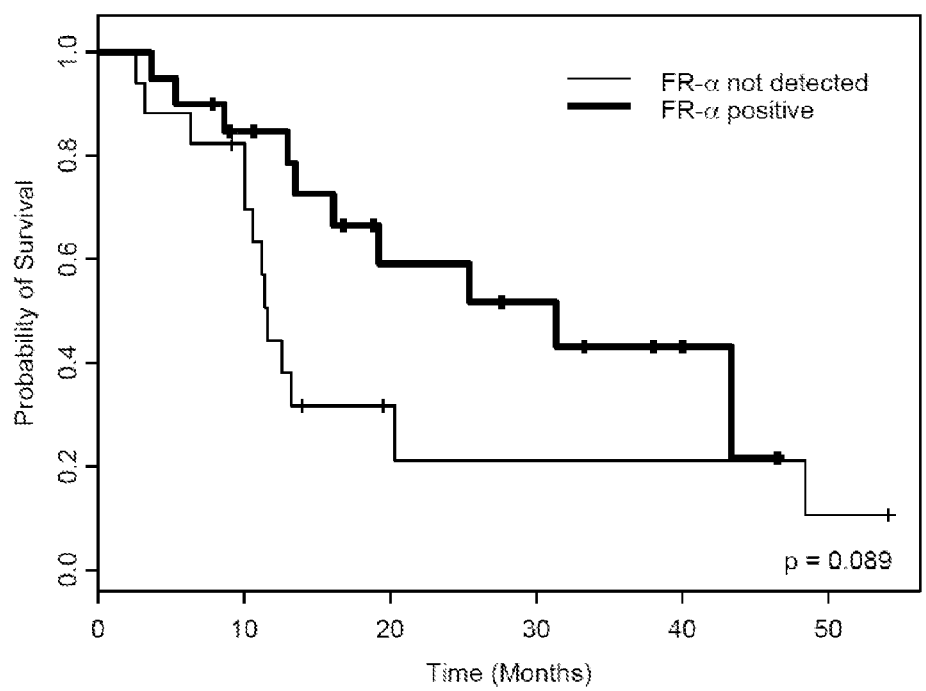
FIG. 2 shows the overall survival curve for patients whose tumor cells express detectable levels of the FR-α protein. Such patients have only a slightly greater probability of longer overall survival than patients whose tumor cells do not express detectable levels of the FR-α when treated with the therapeutic combination of pemetrexed and cisplatin.
Figure 3:
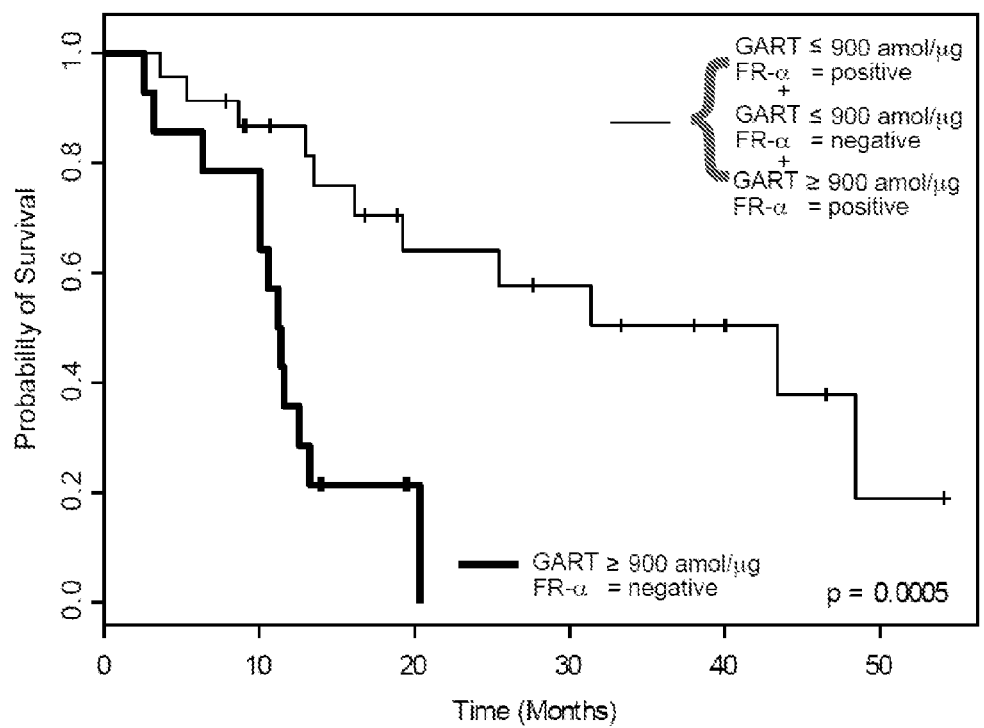
FIG. 3 shows that patients whose tumor cells express detectable levels of the FR-α protein and whose tumor cells also express less than 900 amol/μg protein analyzed have a much greater probability of longer overall survival than patients whose tumor cells do not express detectable levels of the FR-α and also express more than 900 amol/μg protein analyzed, when treated with the therapeutic combination of pemetrexed and cisplatin.
Figure 4:
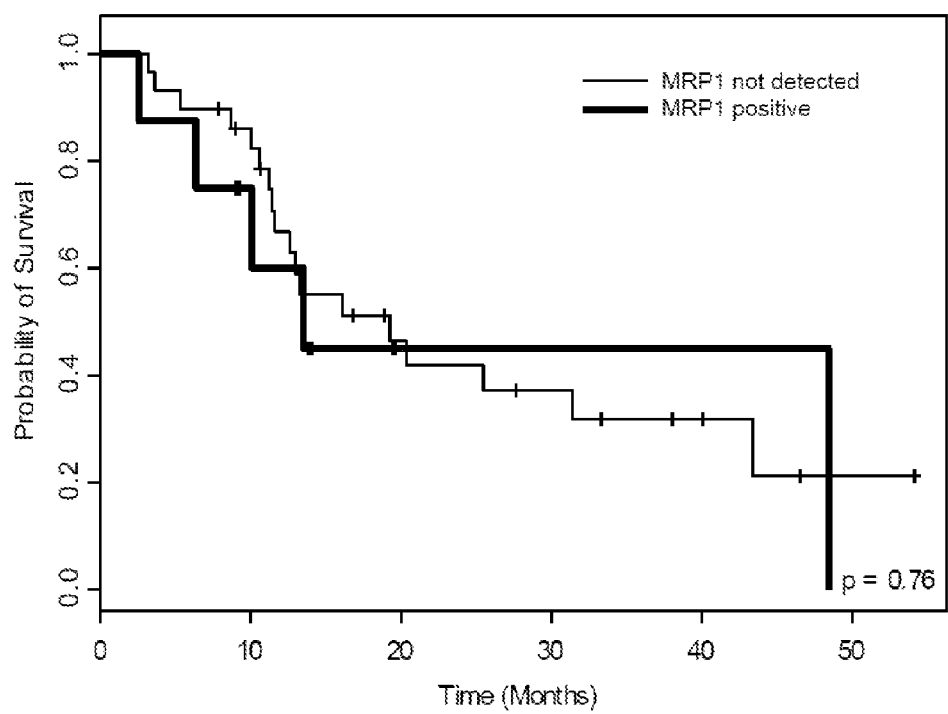
FIG. 4 shows that patients whose tumor cells express detectable levels of the MRP1 protein have no greater probability of longer survival than patients whose tumor cells do not express detectable levels of the MRP1 protein when treated with the combination of pemetrexed and cisplatin.
Figure 5:
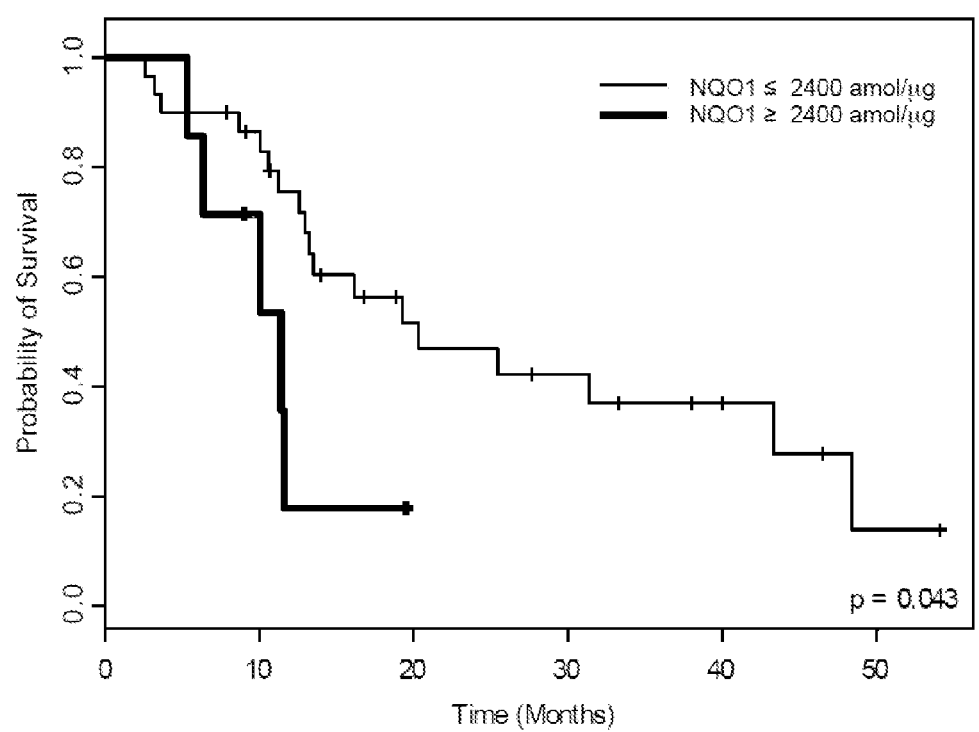
FIG. 5 shows that patients whose tumor cells express NQO1 protein levels below 2400 amol/μg protein analyzed have only a slightly greater probability of longer survival than patients whose tumor cells express NQO1 protein levels above 2400 amol/μg when treated with the combination of pemetrexed and cisplatin.
Figure 6:
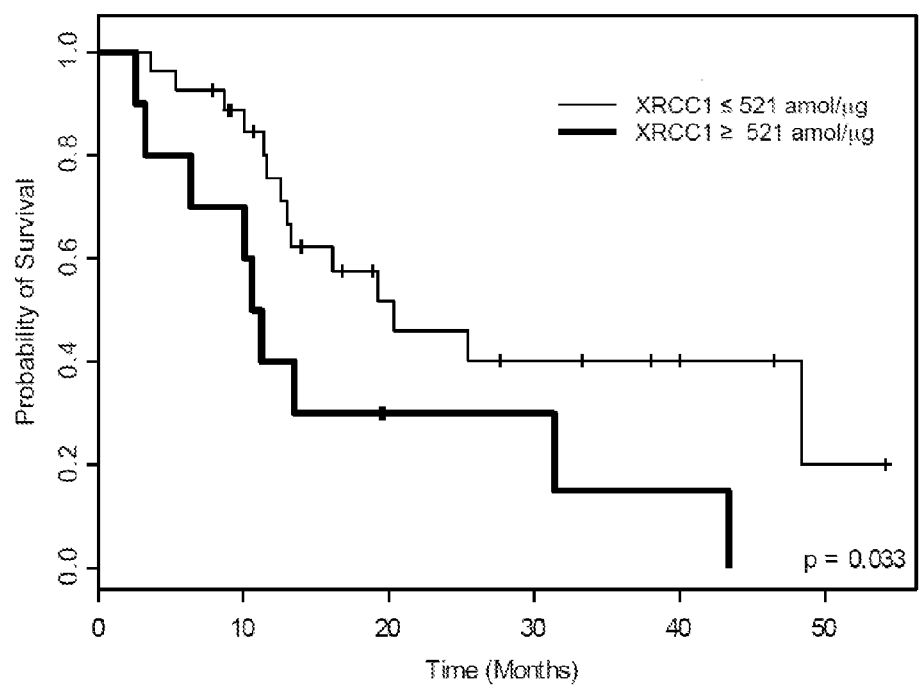
FIG. 6 shows that patients whose tumor cells express XRCC1 protein levels below 521 amol/μg protein analyzed have only a slightly greater probability of longer survival than patients whose tumor cells express XRCC1 protein levels above 521 amol/μg when treated with the combination of pemetrexed and cisplatin.

Quantitative SRM/MRM data across a number of proteins including those proteins specifically targeted by the therapeutic drug pemetrexed indicate a strong and significant correlation of the combinatorial levels of the GART and FR-α proteins with positive therapeutic outcome by treatment of the cancer patient with pemetrexed, as evidenced by extended survival after initial diagnosis and initiation of treatment regime with pemetrexed. The GART protein alone showed correlation (p=0.007) with increased overall survival to treatment with pemetrexed and cisplatin. The FR-α protein alone showed no correlation (p=0.089) with increased overall survival to treatment with pemetrexed and cisplatin (FIGS. 1 and 2). However, the combination of both GART and FR-α proteins demonstrated highly significant correlation (p=0.0005) to increased overall survival in this cancer patient population from treatment with pemetrexed and cisplatin (FIG. 3). Quantitative levels of other proteins did not correlate with a positive treatment outcome to treatment with pemetrexed and cisplatin as evidenced by a lack of extended survival shown in the overall survival curves (FIGS. 4-6).

The invention claimed is:

1. A method of treating a patient suffering from lung cancer comprising:
    (a) quantifying the level of a specified FR-α fragment peptide and the level of a specified GART fragment peptide in a protein digest prepared from a tumor sample obtained from the patient and calculating the level of both the FR-α and GART peptides in said sample by selected reaction monitoring using mass spectrometry;
    (b) comparing the level of said FR-α fragment peptide to an FR-α reference level and comparing the level of said GART fragment peptide to a GART reference level, and
    (c) treating the patient with a therapeutic regimen comprising an effective amount of pemetrexed when the level of the GART fragment peptide is lower than said reference level and when the level of the FR-α fragment peptide is detected, and
    (d) treating the patient with a therapeutic regimen that does not comprise an effective amount of pemetrexed when the level of the GART fragment peptide is above said reference level and the FR-α fragment peptide is not detected.

2. The method of claim 1 wherein said reference level of the GART fragment peptide is 900 amol/μg., +/−250 amol/μg, +/−150 amol/μg, +/−100 amol/μg, +/−50 amol/μg, or +/−25 amol/μg of biological sample protein analyzed and wherein said FR-α fragment peptide is detected above the lower limit of detection or not detected.

3. The method of claim 1, wherein said therapeutic regimen comprising an effective amount of pemetrexed further comprises an effective amount of cisplatin.

4. The method of claim 1, wherein said protein digest comprises a protease digest.

5. The method of claim 4, wherein said protein digest comprises a trypsin digest.

6. The method of claim 1, wherein mass spectrometry comprises tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry.

7. The method of claim 6, wherein the mode of mass spectrometry used is Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

8. The method of claim 1, wherein the specified FR-α peptide has the amino acid sequence as set forth as SEQ ID NO:1.

9. The method of claim 1, wherein the specified GART peptide has the amino acid sequence as set forth as SEQ ID NO:2.

10. The method of claim 1, wherein the tumor sample is a cell, collection of cells, or a solid tissue.

11. The method of claim 10, wherein the tumor sample is formalin fixed solid tissue, and wherein said tissue optionally is paraffin embedded tissue.

12. The method of claim 11, wherein said protein digest of said biological sample is prepared by the Liquid Tissue protocol.

13. The method of claim 1, wherein quantifying the specified FR-α fragment peptide comprises determining the amount of the FR-α peptide in said sample by comparing to a spiked internal standard peptide of known amount, wherein both the native peptide in the biological sample and the internal standard peptide corresponds to the same amino acid sequence of the FR-α fragment peptide as shown in SEQ ID NO:1.

14. The method of claim 1, wherein quantifying the specified GART fragment peptide comprises determining the amount of the GART peptide in said sample by comparing to a spiked internal standard peptide of known amount, wherein both the native peptide in the biological sample and the internal standard peptide corresponds to the same amino acid sequence of the GART fragment peptide as shown in SEQ ID NO:2.

15. The method of claim 13, wherein the internal standard peptide is an isotopically labeled peptide, and wherein said peptide comprises at least one heavy stable isotope selected from $^{18}O$, $^{17}O$, $^{15}N$, $^{13}C$, and $^{2}H$, or combinations thereof.

16. The method of claim 13, wherein detecting and quantitating the specified FR-α fragment peptide can be combined with detecting and quantitating other peptides from other proteins in multiplex so that the treatment decision about which agent used for treatment is based upon specific levels of the specified FR-α fragment peptide in combination with other peptides/proteins in the biological sample.

17. The method of claim 13, wherein detecting and quantitating the specified GART fragment peptide can be combined with detecting and quantitating other peptides from other proteins in multiplex so that the treatment decision about which agent used for treatment is based upon specific levels of the specified GART fragment peptide in combination with other peptides/proteins in the biological sample.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Homo sapiens

<400> SEQUENCE: 1

Asp Val Ser Tyr Leu Tyr Arg
1               5

<210> SEQ ID NO 2
<211> LENGTH: 8
<212> TYPE: PRT
<213> ORGANISM: Homo sapiens

<400> SEQUENCE: 2

Val Leu Ala Val Thr Ala Ile Arg
1               5
```